(12) United States Patent
Talamo et al.

(10) Patent No.: US 10,598,649 B2
(45) Date of Patent: Mar. 24, 2020

(54) DEVICE AND METHOD FOR CERTIFYING THE LIFE CYCLE OF AN ORGANIC PRODUCT

(71) Applicants: FONDAZIONE UNIVERSITARIA INUIT TOR VERGATA, Rome (IT); MIDRA TECHNOLOGIES S.R.L., Rome (IT)

(72) Inventors: Maurizio Talamo, Rome (IT); Silvio Casagrande, Rome (IT)

(73) Assignees: FONDAZIONE UNIVERSITARIA INUIT TOR VERGATA, Rome (IT); MIDRA TECHNOLOGIES S.R.L., Rome (IT)

(*) Notice: Subject to any disclaimer, the term of this patent is extended or adjusted under 35 U.S.C. 154(b) by 248 days.

(21) Appl. No.: 15/755,630

(22) PCT Filed: Jul. 28, 2016

(86) PCT No.: PCT/EP2016/068120
§ 371 (c)(1),
(2) Date: Feb. 27, 2018

(87) PCT Pub. No.: WO2017/036689
PCT Pub. Date: Mar. 9, 2017

(65) Prior Publication Data
US 2018/0246075 A1     Aug. 30, 2018

(30) Foreign Application Priority Data

Sep. 4, 2015   (IT) .......................... UB2015A002727
Oct. 29, 2015  (IT) .......................... UB2015A004781

(51) Int. Cl.
*G01N 33/18*   (2006.01)
*G01N 11/06*   (2006.01)
(Continued)

(52) U.S. Cl.
CPC .......... *G01N 33/1826* (2013.01); *G01N 1/14* (2013.01); *G01N 11/00* (2013.01); *G01N 11/06* (2013.01);
(Continued)

(58) Field of Classification Search
CPC .... G01N 33/18; G01N 33/4905; G01N 11/00; G01N 11/06; G01N 33/2823
(Continued)

(56) References Cited

U.S. PATENT DOCUMENTS 5,172,332 A * 12/1992 Hungerford .............. E03F 7/00
                                                    700/267
5,633,460 A *  5/1997 Manmaru ............... B08B 17/00
                                                    73/170.29
(Continued)

OTHER PUBLICATIONS

Sung et al, "Remote fish aquaculture monitoring system based on wireless transmission technology", IEEE, 2014, vol. 1, pp. 540-544.
(Continued)

*Primary Examiner* — Clayton E. LaBalle
*Assistant Examiner* — Kevin C Butler
(74) *Attorney, Agent, or Firm* — Lucas & Mercanti, LLP

(57) ABSTRACT

The present invention relates to a device that allows the certification the entire life cycle of an organic product. The invention is characterized by four basic aspects: —it allows to carry out automatic samplings to detect the water quality, including that in which fish/shellfish/mussel are bred; the biological liquids (urine), the solute in distilled water, the content of litter of farming livestock; —it checks and guarantees that the sampling system has not been opened or modified; —it generates alarms in real time and keeps track of them, for the purposes of the certification of the agro- (Continued)

alimentary product; —it stores the information/samples in a "black box" accessible only to the analyzing and certifying bodies.

9 Claims, 2 Drawing Sheets

(51) Int. Cl.
| | |
|---|---|
| *G01N 33/49* | (2006.01) |
| *G01N 11/00* | (2006.01) |
| *G01N 1/14* | (2006.01) |
| *G01N 33/00* | (2006.01) |
| *G01N 33/02* | (2006.01) |
| *G01N 33/24* | (2006.01) |

(52) U.S. Cl.
CPC ......... *G01N 33/0098* (2013.01); *G01N 33/02* (2013.01); *G01N 33/18* (2013.01); *G01N 33/1886* (2013.01); *G01N 33/24* (2013.01); *G01N 33/4905* (2013.01); *G01N 2033/184* (2013.01); *G01N 2033/245* (2013.01); *Y02A 20/206* (2018.01)

(58) Field of Classification Search
USPC ........................................................ 73/53.01
See application file for complete search history.

(56) References Cited

U.S. PATENT DOCUMENTS

| | | | |
|---|---|---|---|
| 2007/0122870 A1* | 5/2007 | Turley | G01N 33/1866 435/34 |
| 2013/0174792 A1* | 7/2013 | Delabbio | A01K 63/06 119/200 |
| 2018/0246075 A1* | 8/2018 | Talamo | G01N 33/18 |

OTHER PUBLICATIONS

International Search Report and Written Opinion for International Application No. PCT/EP2016/068120 (9 Pages) (dated Sep. 27, 2016).

* cited by examiner

DEVICE AND METHOD FOR CERTIFYING THE LIFE CYCLE OF AN ORGANIC PRODUCT

CROSS-REFERENCE TO RELATED APPLICATIONS

This application is a 371 of PCT/EP2016/068120, filed Jul. 28, 2016, which claims the benefit of Italian Patent Application No. UB2015A002727, filed Sep. 4, 2015 and Italian Patent Application No. UB2015A004781, filed Oct. 29, 2015.

FIELD OF THE INVENTION

The present invention relates to a device, as shown in FIGS. 1 and/or 2, useful for monitoring and certifying a product of organic crops or farming, through its entire life cycle.

BACKGROUND OF THE INVENTION

Organic agriculture, understood as the set of tools and methodologies used by agri-food production, which meets strict quality requirements of the production chains and of the agricultural products so obtained, cannot disregard the need to demonstrate objectively and continuously that such requirements have been met throughout the whole life cycle of the "organic product."

"Organic product", in accordance with the present invention, means and includes any product of plant, animal or fish origin that is used for human food and that is produced in a way that complies with official standards set by national governments and international organizations. Marketing food with the "organic" label is, in fact, regulated by governmental food safety authorities, such as the US Department of Agriculture (USDA) or European Commission.

In particular, by organic fish product we shall mean the product of fish farming in ponds, lakes or sea areas in "bays" (e.g "fjords" type), in which it is possible to place the device according to the invention on the ground and the water extraction pipes into the sea/lake/ponds.

It is apparent that, by means of appropriate technical modifications well known to the skilled in the art, it is possible to adapt the system according to the invention for use within "fences" in the open sea, within which the breeding of fish is carried out. This latter aspect is not to be underestimated, because, while it is very easy to make extractions on land or breeding ground fences, it is very difficult to control the type of "feedstuff" that is administered to fish in the sea.

Normally, the control tests on farm land, on a farming system or on the feedstuff used, are applied randomly by making sample extractions and performing the analysis on the samples themselves.

Furthermore, producers may also self-certify the quality of their production systems. These two methods give rise to different problems, in fact, on one side, the sample control is meaningful for the public, only if there is a negative result and, on the other side, the self-certification is not usually perceived as credible by consumers or consumers' associations. The device in accordance with the present invention overcomes these "technical problems."

DESCRIPTION OF THE INVENTION

The present invention provides a solution to the previous problems, by allowing the continuous and timely monitoring (for subsequent certification) of the quality of the micro environment fundamental elements (water, soil, stable, pond, etc.), during the entire life cycle of any product of organic agriculture or farming.

Figure 1:
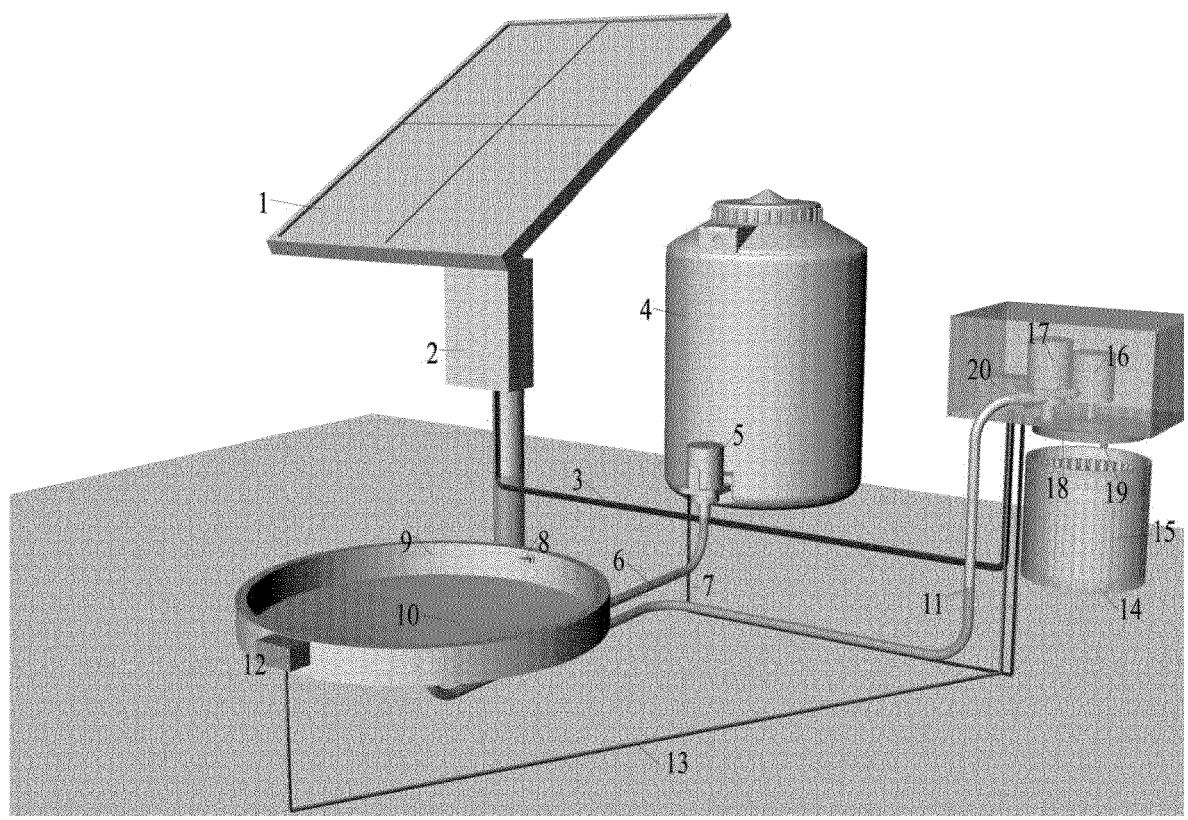
FIG. 1: it is a schematic representation of the device of the invention, comprising the following parts:
at least one solar panel (1);
at least one charge controller and buffer battery (2);
at least one main power cable (3);
at least one distilled water tank (4);
at least one distilled water pump (5);
at least one container (9) for sample collection (sample collection container);
at least one tube (6) to run distilled water into the container (9);
at least one power cable (7) for the distilled water pump;
at least one irrigation nozzle (8) for the container (9);
at least one filtering net and water opacity, acidity and bacteriological purity sensors (10);
at least one water collection pipe for water analysis (11);
at least one motion and level sensor (12);
at least one data cable (13) for connecting the sensors with a control system;
at least one cylindrical container (14) of test tubes (15) (test tubes container);
at least one test tube (15);
at least one stepper motor (16);
at least one pump (17) for collecting samples;
at least one rotating funnel (18);
at least one nozzle (19) for filling the test tube (15);
at least one electronic control system, the system clock (20);
optionally at least one watertight box for the positioning of the device in the water, anchored to the soil.
Figure 2:
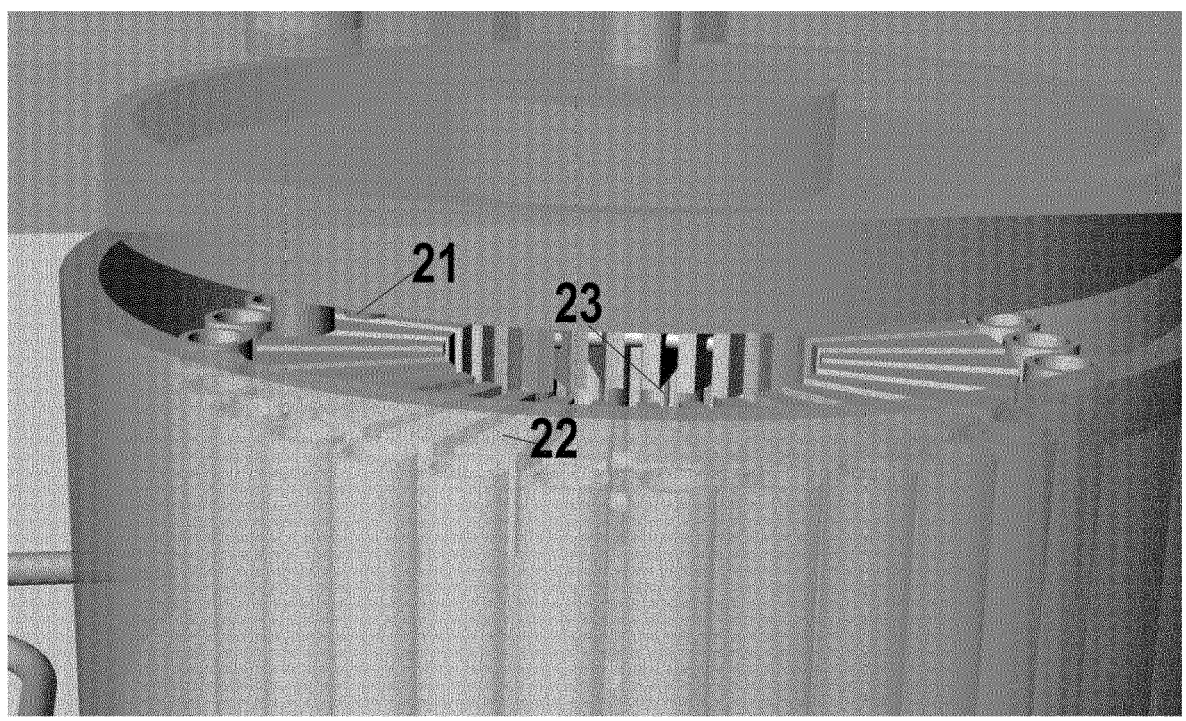
FIG. 2: it is a schematic representation of the cylindrical container (14) of test tubes (15), including a schematic representation of its internal part, in which the housings for the test tubes are also shown; optionally, the cylindrical test tubes container also comprises:
at least a water quality sensor made of graphene (22);
at least one nozzle irrigation (21) for sensors in graphene (22); and
at least one connection cable (23) to the sensor in graphene (22).

It is therefore object of the present invention the device, as shown in FIGS. 1 and 2, useful for monitoring and certifying of an organic production process and/or product; comprising the following parts:
at least one solar panel (1);
at least one charge controller and buffer battery (2);
at least one main power cable (3);
at least one distilled water tank (4);
at least one distilled water pump (5);
at least one container (9) for sample collection (sample collection container);
at least one tube (6) to run distilled water into the container (9);
at least one power cable (7) for the distilled water pump;
at least one irrigation nozzle (8) for the container (9);

at least one filtering net and water opacity, acidity and bacteriological purity sensors (10);

at least one water collection pipe for water analysis (11);

at least one motion and level sensor (12);

at least one data cable (13) for connecting the sensors with a control system;

at least one cylindrical container (14) of test tubes (15);

at least one test tube (15);

at least one stepper motor (16);

at least one pump (17) for collecting samples;

at least one rotating funnel (18);

at least one nozzle (19) for filling the test tube (15);

at least one electronic control system, the system clock (20);

optionally at least a water quality sensor made of graphene (22);

optionally at least one nozzle irrigation (21) for sensors in graphene (22);

optionally at least one connection cable (23) to the sensor in graphene (22);

optionally at least one watertight box for the positioning of the device in the water, anchored to the soil.

According to an embodiment of the invention, the solar panel (1) is sized so as to ensure full recharge of the battery during the daylight hours and at the same time to meet the energy demand of the various electronic components of the system (pump, stepper motor, sensors, electronic system control, system clock) and it is connected to a charge controller for the protection of the battery in case of excessive or insufficient charge situations, thus ensuring maximum durability.

The battery (2) is sized so as to guarantee the night power needs of the system, or in case of low solar energy availability, for example during the days with unfavorable meteorological conditions. For a basic installation, such as the one shown in FIG. 1, it is preferable to provide a solar panel from 30 W to 50 W, a charge controller 5 A-PWM and a 12V battery from 18 Ah to 24 Ah.

The tank for the distilled water (3) must be made of rigid material and such as to ensure the maintenance in time of the chemical and physical characteristics of the distilled water contained in it, even in case of outside installation or direct exposure to sunlight, for this purpose small polyethylene tanks for drinking water can be used. The tank is equipped with vent and plug with seal. The volume of the tank is determined by the average quantity of water required for a full collection cycle; this quantity varies depending on the solubility of the material to be analyzed, that is collected on the filtering net, by the number of collection cycles and by the period of autonomy, which is to be ensured to the system. For the system presented in the following Example 1, and represented in FIG. 1, in which the collection material is constituted by averagely clay soil and the sampling is performed once a day, the system can be autonomous for a month with a tank capacity from 30 liters to 60 liters.

The pump for distilled water (5) mounted at the base of the tank is a centrifugal pump capable of drawing water from the reservoir and pushing it in the distilled water feed pipe (6) at such a pressure as to allow the outflow of a jet from the irrigation nozzle (8) behind the filtering net (10), such jet being powerful enough to flush and dilute the material on the net itself. If the installation allows the mounting of the pump to the base of the tank it is not necessary that the pump be self-priming.

The tube of distilled water (6) connected with the sample collection container (9), like all the other tubes in the system, must be of a flexible material and at the same time such as to ensure the maintenance of the chemical and physical characteristics of the liquid flowing inside them.

The irrigation nozzle (8) for the sample collection container (9) serves to allow the spillage of the distilled water jet so that it can be distributed as evenly as possible on the collection net of the material.

The sample collection container (9) is made of plastic material, sufficiently resistant, with characteristics such as to ensure the maintenance of the chemical and physical characteristics of the material collected in it and in turn not to be altered by the materials collected in it. Its purpose is to collect on the filtering net (10) the material to be analyzed and, during the sample collection cycles, the distilled water mixed with the collected material, which we will define the collection liquid, obtained as a result of the irrigation of the net. The sample collection container must therefore ensure a sealing such as to allow the retention of the collection liquid for all the time necessary for sensors to analyze the collection liquid for opacity, acidity and bacteriological purity, housed in its interior.

The filtering net (10) must have a mesh sufficiently dense to avoid that during the spraying cycle debris falling inside the sample collection container (9), together with the collected liquid, could clog the tubes or the nozzle for filling the test tube (19).

The sensors for opacity and acidity are a set of electronic sensors consisting of:

an optical sensor that uses an infrared beam to measure the opacity of the collection liquid;

a pH-meter equipped with a pH probe to measure the acidity of the collection liquid;

optionally a sensor in graphene can also be mounted here for the analysis of bacteriological purity of the water; since such a sensor must be regenerated after use by washing or heating, if inserted, this sensor must be equipped with a heating system (a micro coil realized in high impedance and strong resistance to high temperature material, e.g. nickel-chromium alloy) activated by the electronic control system in response to each reading; the presence of this additional sensor allows to carry out complete cycles of analysis of the samples prior to sampling and therefore determine from time to time whether or not to proceed with the filling of the test tube.

The collection pipe of the water to be analyzed (11), like all the other pipes in the system, is made of flexible material and at the same time such as to ensure the maintenance of the chemical and physical characteristics of the liquid flowing inside it.

The motion and level sensor (12) applied to the sample collection container allows to generate alarms in the event of tampering with the system. The alarms are listed by time and collected by the electronic control system.

The cylindrical container (14) of test tubes (15) consists of a cylindrical vessel, in which are inserted a series of laboratory test tubes, a series of sensors in graphene and a rotating funnel equipped with two nozzles connected to a stepper motor. The test tubes (15) are of round cross-section and the center of the mouth of each tube is positioned at a predetermined distance A from the center of the cylinder and at a constant distance B from the center of the previous test piece and the next; a closed loop of test tubes equidistant from one another is thus created. Also the sensors in graphene are arranged in a circular manner in a closed loop and are equidistant from each other.

The initial position of the rotating funnel provides that the filling nozzle is positioned at the center of the test tube no 1 and that of the irrigation for the sensors in graphene over sensor in graphene no 1. At the end of each sample collection the stepper motor, to prepare for the next collection system, rotates the collection funnel of x degrees calculated according to the following formula:

$$\frac{\text{Number of test tubes}}{360}$$

The number of test tubes and sensors in graphene depends on the autonomy, which is intended to be given to the system and on the size of the test tubes, of the sensors and of the collecting cylinder. The base of the cylindrical test tubes container is perforated so as to allow the overflow of any collection liquid surplus.

The stepper motor, contained in a waterproof box positioned at the top of the cylindrical test tubes container, allows to reach a very high level of precision in the positioning of the collection nozzles in the center of the test tube and the sensor, the motor shaft protrudes from the base of the box, in which the motor is contained and is inserted inside the cylinder from the top, in order to be connected to the rotating funnel. The motor is placed so that the center of the motor shaft coincides with the center of the cylinder and of the rotating funnel. The movements of the stepper motor are coordinated by the electronic control system.

The pump for collecting samples (17) is a self-priming pump located above the cylindrical test tubes container. Operated by the electronic control system the pump allows the collection of liquid present in the sample collection container to be aspirated and transferred into the rotating funnel.

The rotating funnel (18) is connected directly to the shaft of the stepper motor and equipped with a nozzle (19) for the filling of the test tube and an irrigation nozzle (21) for the sensors in graphene respectively positioned at distance A from the first center of rotation of the funnel (equal to the distance of center of the test tubes from the center of the cylinder) and the second in such a way as to optimize the wetting of the graphene surface of the sensor avoiding at the same time spraying also the neighboring sensors. For each sampling the electronic control system will make the funnel rotate by x degrees, in such a way that the nozzles are already positioned for the subsequent collection. When the nozzle is positioned at the center of the test tube, the liquid drawn by the pump for collecting samples is transferred into the rotating funnel and from here through the nozzle ends up directly inside the test tube, the eventual excess of liquid comes out from the test tube and is dispersed in the soil below the cylindrical test tubes container. The same occurs for irrigation nozzle for the sensors in graphene, the sensors being mounted in such a way as to allow the outflow of the excess liquid.

The water quality sensors realized in graphene (22) are made in a form such as to allow assembly of the closed-loop sensors, while exposing at the same time as much surface in graphene as possible to the spraying liquid. The sensors are electronically connected to the electronic control system of the black box.

The electronic control system is electronically connected to the system clock (20), to the stepper motor, the pumps and to all the sensors. Its task is to synchronize all collecting operations and to detect and store the data provided by the sensors.

The watertight box (in "marine" steel or other suitable material; well-known and easily made by the skilled person in the field) for positioning the device in the water, anchored to the soil and at any desired height above the soil, is provided with:

- suitable rings which bind one or more ropes/chains of the mooring post (rope/chain tied to the seabed) and/or of the surface buoy for the recovery of the device by the certifying bodies;
- suitable watertight through holes, where to pass electrical cables such as those of the solar panel and/or of the transmitting/receiving data antenna, and other cables/utilities, if necessary;
- of taps/solenoid valves/tube holder etc., provided with suitable check valves, if necessary, for the drawing and spillage/ejection of liquid/samples;
- suitable sample collection system, in which the sample is injected into the test tube closed with a watertight rubber/soft material plug easily pierceable by a sample transfer needle; this last embodiment is easily implemented on the device according to the invention, by an average expert of the art, by adapting/modifying suitably the operating system.

The Operation Flow is the Following:

1: activating the distilled water pump (5) for washing the collection net;
2: reading the data from sensors for opacity and acidity (10);
3: reading from system clock (20) of the timestamp (time/time of withdrawal or alarm) to be associated to data collected by the sensors;
4: storing the data received from the sensors (10) on a memory, persistent in case of lack of electrical supply, installed in the electronic control system (20);
5: generating alarms in case of contamination;
6: activating the pump for sample collection (17) for transferring the liquid in the test tubes and on the sensors in graphene;
7: reading the data from the sensors in graphene (22);
8: reading from system clock (20) of the timestamp to be associated to data collected by sensors in graphene;
9: storing the data received from the sensors in graphene (22) on the permanent memory;
10: generating possible alarms in case of contamination; and
11: activating the stepper motor (16) for the x degrees rotation of collection funnel.

The system is constantly waiting for any signals from the motion sensors and level (12), in case the sensors indicate an abnormal handling of the sample collection container, the data are associated with the timestamp and stored on the memory and the system generates an alarm.

The Device According to the Invention has the Following Requirements:

- it operates continuously checking the quality of the microenvironment for all the time that the process of farming or breeding requires to provide a product;
- the verification process is a "third party", i.e. the infrastructure, that continuously controls the microenvironment, is completely independent and does not require external power supplies; it uses a black box model (the black box will be also indicated hereinafter with the term "central element") to acquire the information during the observation period, that only the certifier can acquire;
- the system is able to autonomously detect whether abnormalities have occurred, such as: displacement of the control sensors, bypass of irrigation systems, etc.;

the system is able to provide, in the black-box mode, this information to the certifier and in this way the device according to the invention allows to achieve the goal of being able to demonstrate that the quality of the microenvironment is the one certified by the sensor system for the entire period of production/monitoring;

the elements (14) (the cylindrical test tubes container), (15) (the test tubes), (16) (the stepper motor), (17) (the pump), (18) (the rotating funnel), (19) (the nozzle), (20) (the electronic control system and the system clock), with the addition of a CPU, a Wi-Fi device, a permanent memory for the protected data, a secure permanent memory for the program, a cryptoengine (cryptographic accelerator) for encrypting and decrypting operations, constitute the central element (hereinafter also indicated with the term "black box") according to the present invention;

the elements (6) (the tube of distilled water connected to the sample collection container), (11) (the collection pipe of the water to be analyzed), (8) (the nozzle), (9) (the sample collection container), (10) (the filtering net and sensors for opacity, acidity and bacteriological purity of the water), (12) (the motion and level sensor), (13) (the data cable for connecting sensor) can be duplicated allowing measurements at different places of the soil (or on the dirt floor of a stable, etc.). In this case, the elements (6) and (11) are each supplemented with an electronic valve, controlled from the central element, to block the flow of water. Two additional valves allow to put in direct communication the parts in common of the element (6) with the element (11). These shared portions of the tube, before each measurement, are washed, putting them in communication through the latter two valves, with the water of tank (4).

Operating Method

Specifically the invention is constituted by a circuit that acquires in a continuous manner:

minimum quantity of liquid from the irrigation systems and outflow of waste water (pickup sensors);

information on the content of small portions of land (irrigation and sampling sensors);

information about correct placement of irrigation and sampling sensors;

timestamp (date and time at which the sample was taken) associated with each alarm or detection performed (an internal clock, always powered with buffer battery, provides timestamps).

All the data, samplings and alarms are collected in a central element (black box) that can be opened only by the certifier or by the laboratory analyzing the samples.

The elements of the circuit outside the central object (irrigation and sampling sensors carrying out the samplings of water on the soil) are protected by motion and tilt sensors.

In the central element there are multiple test tubes that allow for multiple samplings, keeping them separated from each other in order to be able to verify the evolution of the water quality on the soil.

To each test tube a time stamp obtained from the system clock is associated showing the instant in time, at which the sample was taken, and the identifier and the position of the sampling sensor, from which the sampling was made.

The presence of a solar panel ensures the continuity of the energy required by the electronic and electrical components of the invention. The buffer battery is recharged by the solar panel to avoid losing time certification of the events and samplings.

The movement control system, the calculation component of which is performed in a physically protected manner in the central element, provides objectivity to the measurements and to the effected samplings in that, once the irrigation and sampling sensors are positioned on the ground and the system has been activated, their every move or tilt change is saved by the system as an alarm and is indicated as a visual alarm (a red led, located on the central element, starts flashing).

The system is connected to a set of motion, proximity and pressure sensors comprising, among others, a gyroscope, a magnetometer, an accelerometer, a proximity sensor, a barometer and a pressure meter, which enables the certification of the quality of the culture.

The variations of the flashing frequency allow the farmer to understand which of the sampling sensors was moved: a constant frequency: pulse detector n. 1; two closely spaced pulses: detector n. 2; three closely spaced pulses: detector n. 3, etc.

To make the quality control of the microenvironment, the system activates, at periodic intervals, the irrigation and sampling sensors.

In particular, for the sampling sensors, it triggers a suction pump connected to the sampling sensor, selects a test piece not yet used, and transfers water into the tube.

For the irrigation sampling sensors, it triggers a pump to bring pure water from a tank (always positioned in the central element) to the irrigation sensor and, subsequently, activates the suction pump to make the sampling of the filtered water from the soil, in order to measure the level of purity and quality after being in contact with the ground.

During the sampling, a minimum quantity of water is used by the central element for the purity measurements that are carried out in real time through a set of sensors (to carry out opacity, acidity, presence of harmful substances measurements). These measurements are therefore made directly on site, working proactively and enabling to anticipate problems that, if not addressed in time, could undermine the entire life cycle of the product. The invention, therefore, after being installed in the ground, produces, using the information (roughly) obtained from the sensors, its own "water print", which later will be compared with periodic measurements made by the invention and which will enable the alarms to be generated on variations of said prints that should be detected in the short/medium term.

To create such a print it is not necessary make the same analysis that are to be carried out to certify the quality of water that require a very high detail on the presence and amount of pollutants or hazardous substances from the biological point of view: the sensors (which may be "low-cost" sensors) will be used essentially as qualitative indicators, rather than quantitative, to allow the control component of the invention to compare the prints of the water, in order to generate alarms in time to correct the problem. For example: if the water quickly becomes acidic, we should not wait for laboratory analysis to take action and it is not necessary to calculate the precise level of acidity. The sensor of acidity will only measure that the acidity of water has increased, in order to be able, if necessary, to report the fact with an alarm.

Among other things, the black box encloses and protects encrypted permanent memories as reported below:

the data acquisition component, security and control: CPU, cryptoengine, Wi-Fi device, volatile memory, permanent memory and protected data, permanent and protected memory of the program (machine code), ports of the I/O, to which the sensors and actuators are connected (electromagnetic valves, pumps, heating elements, stepper motor, mechanical control sensor for the opening of the black box, water and microenvironment quality, motion sensors, acceleration sensors, displacement sensors of the magnetic field, alarm LED, stainable surfaces dynamically with colors and textures);

the physical storage component of samples object of measurement: test tubes.

The opening of the black box can be performed exclusively by authorized personnel (in possession of the opening keys of the black box, with which the mechanical opening of the box is made) and each opening is recorded along with the date and hour, in the protected memory of the data. All this creates a burglar resistant mechanism that prevents and/or reports the illicit opening of the black box.

The protected memories are erasable only by using a cipher key defined at the time of the first initialization (construction) of the black box and are in sole possession of the manufacturer.

The control algorithm executed by the black box and stored in the protected memory of the program is described here below:

1) the manufacturer of the black box, for each black box, performs the first initialization by defining:
    a. a unique serial number S1;
    b. a cipher key C1 (unique) to be used exclusively for the initialization operations, which remains in the possession of the manufacturer;
    c. a cipher key C2 (unique) to be used for the operating configuration of the black box—this key is used by the staff in charge of the installation of the device in the appropriate site, which deals with the configuration of the communication channels and which periodically accesses the black box to withdraw the test tubes and insert new ones; and
    d. a key figure C3 (unique) to be used for Wi-Fi communication;
    e. each black box has different S1, C1, C2 and C3;
    f. serial number and cipher keys are stored directly in the permanent protected program memory, so as to be legible only, when the program is running;
    g. the protected permanent storage of data is completely emptied and is written in encrypted form, with:
        C1 key date before initialization,
        C1 key the string "STATUS 0" followed by the date of first initialization;
    h. the program that is saved in the permanent protected program memory of the black box uses the Wi-Fi device to present itself to external clients in WEB mode (http and html). The dialogue with the program running in the black box then takes place directly through a browser that connects to the Wi-Fi of the black box;

2) operative initialization of the black box (it is done at the factory or by an operator directly at the site of use (e.g. a farm), with all connected sensors and the active power); as soon as the power supply is activated, the program present in the protected memory of the black box program is put into effect: it enables Wi-Fi and prepares to receive requests from browser clients on Wi-Fi communication with C3 security key.

We will report the operations that should be performed in this connection.

a. Operations that can be Performed by the Black Box in "STATUS 0"
    i. In order to check whether the system is in operative initialization phase, the operating program running on the black box (henceforth "the program") deciphers key C1 the status string to be, once deciphered, equal to "STATUS 0" or "STATUS 1" or "STATUS 2".
    ii. The operator responsible for operative initialization of the system executes in its own browser, connecting via Wi-Fi to the black box using the C3 key.
    iii. Via the browser, the operator sends the string "CONFIGURATION" and its ID. The program, on receipt of these two information:
        I. If the "CONFIGURATION" has been requested, the "program" stores in the secure permanent storage of the timestamp data (date, hour, minutes, seconds and milliseconds) of the configuration operation and of the operator identifier, who requested it (each configuration task will be saved in protected memory of the data; in this way, it is always possible to know how much, when and by whom the configuration operations have been carried out).
        II. The "program" performs a check of the various components of the control system (plug & play), in order to identify what type and how many sensors are connected to the I/O ports, if the actuators and other devices work properly.
        III. The configuration so read is stored in the secure permanent storage of data, encrypted with the key C2 and transmitted to the PC of the operator, who, via browser, saves it into PC's file system, for the purpose of documentation of operating configurations of the black box.
        IV. The "program" files with key C1 the new state of the system and makes it "STATUS 1", always associating a timestamp; it waits for the next request by the operator, which request should be: "Measurements."

b. Operations that can be Performed by the Black Box in "STATUS 1"
    i. The operator responsible for operative initialization of the system executes its own browser, connecting to Wi-Fi to the black box using the C3 key. Via the browser, the operator sends the string "MEASUREMENTS" and its ID. Upon receipt of these two information items, if "MEASUREMENT" has been requested, the program receives from the operator, always through the browser:
        I. for each type of sensor, the periods to be used for making the measurements that require the storage of the sample in the test tubes;
        II. for each type of sensor, periods to be used for carrying out the control measures of abnormal conditions, whose samples are deposited in the test tubes only in case anomalous values are detected that generate alarms;
        III. the polling periods of all the displacement, acceleration, magnetic field variation sensors;
        IV. this configuration information is filed with the key;
    ii. At the end, the program is placed in "STATUS 2", by storing in the permanent protected memory with the key C1 the string "STATUS 2" linked to the time stamp of the status change.

c. Operations that can be Performed by the Black Box in "STATUS 2"

When in "STATUS 2", the program is working in the normal operating cycle. During this cycle the program:

1. checks in polling with a period provided at configuration time and stored in the secure permanent storage of data that the positions on the ground of the black box, the sensors, the filtering nets have not varied;
2. performs periodic measurements, both by saving samples and without saving samples, storing in the permanent protected data memory the results of measurements carried out and the timestamp;

3. handles the available variations in power, activating with greater or lesser frequency its components (variation of the polling and measurement periods);
4. indicates by colors, textures, Wi-Fi flows and so on, the data relating to the history of the measurements carried out;
5. always reports via Wi-Fi alarm conditions, relating to both safety (movements) and availability of test tubes.

In case of security alarms, the black box stores permanently the alarm data (time, reason). During security alerts all measurements proceed, but they are accompanied by the alarm information. In the case where it is a multi-sensor system is in this way possible that one of the detectors goes into alarm due to a change of position, but the others continue to provide reliable information that is detected and stored in the black box.

In presence of alarm for "test tubes shortage" or "distilled water shortage" or other, the system blocks its operations and prepares to receive the consent after an operator has replenished the depleted assets.

An operator connected via the browser, when the black box is in the "STATUS 2", receives immediately the following:
  I. Active safety alarms;
  II. Active asset depletion alarms;
  III. Overall status of the measures carried out.
Via browser, the operator can:
1. Reset the safety alarms. The operation is stored in the secure permanent data storage and from this moment on the measurements of the sensors, for which the alarms have been reset, will be considered and marked as valid once again.
2. Indicate (by encrypting the request with key C2) that he is opening the black box to restore a depleted asset (distilled water, test tubes or others). When the asset is restored the alarm automatically disappears.
3. Indicate that the normal operating cycle can start again because the asset has been restored and the black box closed.
4. Modify the periods of measurement and polling (as in "STATUS 1")
5. Discontinue the black box functioning (e.g. for shifting or bringing it at the factory), using the C2 key to encrypt the request.

All the requests are encrypted with the key C2, the controls are provided interactively as they are presented on the operator's browser. All requests are stored in the secure permanent data storage and encrypted with the key C1.

The device according to the invention is characterized by three basic innovative aspects that are not present in any competitors' product on the market:
  allows for automatic withdrawals in order to assess the quality of the water (and the soil, on which the water flows); measurements are therefore objective, timely, multiple and spread on the ground;
  monitors and guarantees that the collection system has not been opened, modified or moved from its original location and that samples continue to be always taken at the same point, where the items used in the collection have been placed at the origin. The measurements are therefore certain, replicable and certifiable. By installing the invention in several places, attempts at fraud are completely eliminated. The user (e.g. the farmer) can thus demonstrate that throughout the organic product life cycle the water quality has never fallen below the values defined by the regulations;
  generates real-time alerts and keeps them tracked for the organic product quality certification purposes, allowing to face in good time the situations that could lead to degradation of production and the loss of quality certification.

When making a measurement, it must be always possible to demonstrate:
  when this measurement was carried out;
  where it was carried out; and
  how it was carried out.

The invention is based on the idea of incorporating in a single device a measurement system that is certifiable with respect to these three requirements.

The invention is therefore based on:
  a system for the automatic taking water samples filtered from the soil, in which the various samplings are classified temporally, cannot be replaced with fraudulent intent and it is possible to transfer them into a safe way to analytical laboratories that need to evaluate them;
  a motion sensor system (including the "level" sensors) that ensure the inalterability in time of the positions on the soil, where the measurements are taken; thus fraud by malicious operators is avoided and the producers in good faith are guaranteed with respect to the maintenance of water quality levels in the places of the soil considered most critical at installation time;
  a system of sensors (e.g. low-cost sensors) for real-time generating alarms on the negative variations in water quality, in support of the daily operation of users (e.g. farmers) enabling them to work proactively, thus anticipating problems or critical situations;

During the entire life cycle of a product of organic farming, the device according to the invention will ensure and certify that the levels of water quality are constantly kept in accordance with the required standards and that the producer cannot, even fraudulently, change the readings.

It must be noted that the invention can be applied to very different contexts:
  vegetable production, in which it is essential that the water quality is maintained constant throughout the growth period;
  animal breeding, in which it is essential to check the level of "health" of the soil and the micro-environment (stable floor, litter, etc.), on which these animals live (and possibly graze), indicating with alarms the uncontrolled increase of waste water or other liquids, which might affect the proper development of the animals.

The water quality sensors may use graphene as active element: in the state of the art sensors are available made by multifunctional graphene, which, appropriately doped, when placed in contact with an aqueous solution, are able to determine the presence of organic/inorganic substances (the optimal operation is obtained in the presence of inorganic substances) that have been predefined in the doping step. Graphene produces an electrochemical signal that is read by a chip and interpreted. The innovation introduced by the present invention, in relation to this type of sensors, allows its use in open environments. In particular, to the state of the art, the device in graphene should be used in controlled environments (labs), since, after use, graphene must be restored for its subsequent use. This can be done by raising its temperature above 200° C. for a certain time and/or using a swab moistened with distilled water or equivalent solution to clean its surface.

According to the present invention the sensors, including those in graphene, have the following functions:
1. they generate alarms;
2. they analyse part of the samples, the remaining part being discharged into test tubes, allowing, a posteriori, to certify the data recorded by the sensors, thereby eliminating the problem of the volatility of the measures carried out exclusively by means of sensors.

The sensor control program (algorithm) verifies, acquiring data that the network of sensors is not tampered with. This task is performed with a periodicity such as to ensure, in normal operating conditions, the similarity of the performed measurements. Thus, if a measurement cannot be obtained (sensor breakdown) or if it is very different from the last reading performed by the sensor and on the same piece of soil, the sensor control program goes into alarm mode, indicating a fault/malfunction.

The sensor control program (algorithm) synchronizes the current test tube with the data acquired through the sensor: the measurements made by the sensors are checked periodically by the control algorithm. In shorter periods of time measurements are made on samples that, unless the measurement generates an alarm, are not discharged into test tubes. These measurements are designed to verify whether the system has been intentionally or unintentionally tampered with and if there have been no sudden changes in the quality of the soil or the microenvironment under control. With lower frequency, depending on the number of test tubes available, the need for certification, etc., the samples are deposited into test tubes present in the black box. In this case the control algorithm associates the measurement taken at the number of the test tube, in which the sample has been deposited, to enable any control checks. The measured values are secured (signed) in the permanent memory of the black box.

The task of sensor control algorithm is to ensure the restoration of the sensors of the sample collection container, in order to enable the performance of new measurements. As previously mentioned, a sensor in graphene can be "cleaned" by heating it to 200° C. or washing it. The innovative idea is that sensors in graphene of the sample collection container are cleaned using the two techniques in an integrated manner:
1) heating the sensor via a micro-coil made of a material having high impedance and strong resistance to high temperature, (ex. nickel-chromium alloy) with consumption of electrical energy compatible with the powers involved for this purpose;
2) washing with distilled water during the cleaning of the sample collection container, applied to all types of sensors.

The cleaning cycle can be repeated, if the control algorithm verifies that the sensor has not been cleaned completely; after a measurement the cleaning cycle is always carried out.

In parallel to the measurements, the control system sends the captured data using various methods of transferring information. These can be:
1) standard mode, such as Wi-Fi communications at different frequencies available for this purpose;
2) innovative methods, in particular the measurement data are transformed into a variation pattern of a part of the surface of the black box, possibly exposed upward to allow scanning by drones, aircraft, satellites, where the change is either in color or in shape/image (texture). The portion of the surface of the black box used for this purpose is thus exposed and can be examined both through visual inspection of the user (e.g. the farmer or an attendant), or through drones equipped with camera that are sent for inspection of the various black boxes installed at a farm, or, finally, through satellite images (acquired from airplane or satellite) that, analyzed periodically, allow to detect the color and texture of small surfaces. The fact that the passages from both satellite and drone take place asynchronously and with frequency not known in advance, or that the data transmissions take place asynchronously, does not affect the quality of the measurement, since the use of different colors and textures, or the use of auto-identifying communication protocols regarding the data transmitted via Wi-Fi, allows to capture with a single reading all the history of what has occurred in the various measurements carried out by the black box.

These measures, associated with geo-referenced data on the black box, constitute georeferencing quality tag and can be distributed to the web through social networks of free softwares: for example, a service agreement with Google Earth, to create the "layer" "organic farming", would immediately make available to the international community product quality data (shown as both color and texture, and as exact values) by encouraging and supporting the inevitable internationalization of organic farming.

Lastly, the control algorithm that is executed by the black box acts through an acquisition procedure on the basis of times, randomly. The choice of the moment of acquisition, nevertheless below a few tens of minutes, is decided on the basis of the energy capacity available to the central sensor. This allows you to take various acquisition strategies:
  more measurements in the same collection tube;
  execution of the measurements according to the power available at any given time: in low power conditions available, the periods between each measurement, not associated with saving the samples in test tubes, can be extended to ensure in any case the execution of the certification measurements requiring saving samples into the test tubes, measurements necessary for certification by external laboratories.

The control algorithm executed by the black box is described by the following flow:
1—Initialization of the black box: the algorithm performs the control checks of the various components of the system (plug & play), deletes all permanent memories, except for the safety memory, which will report the initialization operation timestamp; the signature and cipher keys are initialized at the factory settings (different for each device and associated with the serial number of the apparatus itself), stored permanently in the safety memory. The initialization can be performed exclusively at the time of the black box installation. From the safety memory it is possible to check how many times and when a black box has been initialized.
2—Operative configuration of the black box: the black box, once initialized, can be reached via Wi-Fi on an encrypted communication channel (SSL or other encrypting techniques), whose cipher key is stored in the safety memory. As first step the black box requires a new cipher key of the communication channel that will be used until the next initialization of the black box or until a security alarm. Using the new cipher key it is possible to configure the periods of the measurements and all other operating parameters of the black box and to indicate to the black box that the sensors and other components of the system have been properly set into the soil.
3—At the end of the operative configuration, the black box blocks access to configuration and starts the normal control and operation cycle. During this cycle the black box that monitors the positions on the soil have not been changed, checks the availability of the test tubes, performs periodic measurements, both saving samples and without saving samples, manages changes in available power, enabling with greater or lesser frequency its components, indicates through colors, textures, Wi-Fi flows and so on the data relating to the history of the performed measurements, it indicates the alarm conditions, both of security and availability of test tubes.

4—In case of alarm the black box becomes available again for variations to the configurations via Wi-Fi, indicating also optically the alarm condition. In the presence of security alarms, the black box stores on a permanent basis in the secure memory the alarm data (time, reason) and is set to receive a new consensus to operate, which will also be stored in the safety memory. During the security alarm all measurements proceed, but they are accompanied by information on the time and the alarm reason. In the event that there is a multi-sensor system, it is thus possible that one of the detectors goes into alarm due to a change of position, but the others continue to provide reliable information that are detected and stored by the black box. The cipher key used during the safety alarms is set back to that of the factory to prevent that a security alarm is operated by an unauthorized operator.

5—If there are alarms for "test tubes shortage" or "distilled water shortage" or other, the system stops its operation and is set to receive the consent after an operator has supplied the exhausted assets. The cipher key is the one set at configuration time.

6—All alarms are in any case stored in safety memory.

7—During normal measurement cycle, all the measurements carried out, both those associated to the tubes and those in which the sample is not deposited in test tubes, are stored on a permanent working memory, which is canceled only during the initialization procedure. In such a memory are also stored all the variations of the cycle, power and all the information relating to non-alarm events.

DETAILED DESCRIPTION OF THE INVENTION

The following examples further illustrate the invention without limiting it.

EXAMPLES

Example 1—Analysis of pH and Heavy Metals Present in the Irrigation Waters of an "Organic" Cultivation In case of irrigation water analysis, the sample collection container is placed under one of the cultivated plants. The plant is chosen based on its position inside the field, preferring the one which, due to the natural terrain slope, receives the major water quantity. A sample collection container having 50 cm a diameter allows the collection of irrigation waters, rainwater and any substances spilled or sprayed directly on the plants themselves (fertilizers, herbicides, pesticides, etc.).

The cylindrical test tubes container is equipped with 30 test tubes and 30 sensors in graphene so as to ensure the system an autonomy of approximately one month; considering the use of approximately one litre of distilled water for each washing, a 50 litres capacity tank is also provided. The control system is set to take a sample once daily. Every morning at 8:00 am, after the irrigation schedule of the field, the electronic control system starts the sampling by turning on the irrigation pump of the sample collection container; subsequently the distilled water is directly mixed to the irrigation water residues and any other possible substances present on the filtering net of the sample collection container.

After 1 minute, in which most of any water-soluble substances have had time to become diluted in distilled water and those non soluble are not yet completely deposited on the bottom of the sample collection container and the acidity and purity sensors have had the opportunity to provide their data to the electronic control system, the liquid is drawn from the collecting pump inside the funnel. The pump is activated for one minute, sufficient time to suck up all the liquids in the sample collection container. During the aspiration the liquid transferred in the rotating funnel is immediately transferred partly inside the test tubes and partly on the surface of the sensors in graphene. Said operation requires about half a liter of distilled water, at the end of the collection the nozzles of the funnel are placed in a point such as not to be aligned to any test tube or any sensor in graphene and another half a liter of water is poured in the system for the cleaning of the same. At the end of the cleaning the system places the nozzles preparing them for the next liquid collection.

In the meantime the control system completes the analysis and classification of the data collected from the samples on the basis of the sampling time.

At the end of the month an operator collects the test tubes and transfers to his own PC the data collected from the electronic control system. These data are subsequently imported in a database and through a management interface it is possible to extract the alarms and the graphs of the measurements made by the sensors.

The alarms and the information about the quality of the water are transmitted in real time through the Wi-Fi interface of the control system (black box) and are displayed (color and texture) on an active surface on the face of the black box pointing skyward. Thus the color and texture values represent a "geotag", since they provide geo-referenced information on the quality of soils and micro-environments under test. The images acquired by the drone and satellite are immediately usable as a "layer" of Google Earth or spread through social networks.

Example 2—Analysis for the Detection of Phyto-Hormones Present in the Soil of Organic Farming The collection was carried out as described in Example 1.

The sensors used are specialized for the detection of phyto-hormones. They were designed by Marshall Porterfield and Angus Murphy of the Faculty of Agriculture at Purdue University and consist of black platinum and carbon nanotubes. They allow to measure in real time the concentration of auxin in different areas of the root surface, following the reaction of the phyto-hormone with nanomaterials, constituting its extremity. The electrical signal generated by the reaction makes it possible to measure the concentration of auxin in a specific point of the root surface.

The alarms are transmitted via the mode Wi-Fi (colors and textures) and can therefore be accessible in real time together with their georeferencing.

The samples object of measurement are stored in the test tubes and taken to the testing laboratory according to the storing criteria set by the laboratory (not more than 48 hours, one week, etc.).

Example 3—Analysis for the Detection of Pesticides Present in the Soil of Organic Farming The collection was carried out as described in Example 1.

The detection time of the pesticide by the specialized sensors (gold-coated magnetic nanoparticles modified with antibodies, which are selective for the chemical component—or the analyte—of interest) are in this case quite long, about 40 minutes.

The alarms are reported in real time, as soon as recorded by the sensors and distributed as in the previous Example.

The collected water sample was taken to the laboratory for analysis in very short times.

Example 4—Analysis of the Liquid Manure of a Cattle Farming of "Organic/Certified Type" for the Detection of Growth Hormones, Antibiotics, Bacteria, Protozoa and Viruses The sampling was performed by taking an aliquot of urine present in the waste liquid manure (installing a pipe from the liquid manure collection to the device of the invention).

The sample taken was brought in very short times to the analysis laboratory.

Example 5—Litter Analysis of a Farm of Poultry (Chickens, Turkeys, Etc.) of "Organic/Certified" Type for the Detection of Growth Hormones, Antibiotics, Bacteria, Protozoa and Viruses The sampling was accomplished by extracting a water aliquot previously poured from the device according to the invention and remained on site for at least one minute, in a concave area of the litter of the livestock. The porosity of the area below the litter box will determine the amount of distilled water that the system will pour in said concave area of the litter box.

The water sample taken was brought in very short times to the analysis laboratory.

Example 6—Water Analysis of Fish Farming in Tanks, Lakes or "Bays" for the Detection of Hormones, Antibiotics/Drugs and for the Analysis of the "DNA" of the Content of the Feed (Dissolved/Present in the Water) Used The sampling was accomplished by sampling an aliquot of water in tanks, lakes or "bays", with the device, which is positioned on the "mainland", through the use of a suitable aspiration "tube".

The water sample taken was placed in test tubes and brought in a short time to the analysis laboratory.

If necessary, the collected sample can be kept at refrigerating (+4° C.) or freezing (−1 to −80° C.) temperature by making appropriate modifications to the device according to the invention.

The invention claimed is:

1. A device for monitoring and certifying the production process and/or product of organic crops or farming, comprising:
   a solar panel;
   a charge controller and buffer battery;
   a main power cable;
   a distilled water tank;
   a distilled water pump;
   a container for sample collection;
   a tube to run distilled water into the container;
   a power cable for the distilled water pump;
   a irrigation nozzle for the container;
   a filtering net and water opacity, acidity and bacteriological purity sensors;
   a water collection pipe for water analysis;
   a motion and level sensor;
   a data cable for connecting the sensors with a control system;
   a cylindrical container of test tubes;
   a test tube;
   a stepper motor;
   a pump for collecting samples;
   a rotating funnel;
   a nozzle for filling the test tube;
   a electronic control system, the system clock;
   optionally a water quality sensor made of graphene;
   optionally a nozzle irrigation for sensors in graphene;
   optionally a connection cable to the sensor in graphene; and
   optionally a watertight box for the positioning of the device in the water, anchored to the soil.

2. The device of claim 1, in which said device is connected to a set of motion, proximity and pressure sensors, comprising a gyroscope, a magnetometer, an accelerometer, a proximity sensor, a barometer and a pressometer.

3. The device of claim 1, wherein the cylindrical test tubes container, the test tubes, the stepper motor, the pump for the collection of samples, the rotating funnel, the nozzle, the electronic control system and the system clock, with the addition of a CPU, a Wi-Fi apparatus, a permanent protected memory for the data, a permanent protected memory for the program, a crypto engine to cipher and decipher operations, constitute a black box.

4. Method of use of the device of claim 1, wherein:
   the solar panel is configured for a power ranging from 30 W to 50 W and is provided with a charge controller 5 A-PWM;
   the battery is 12V from 18 Ah to 24 Ah;
   the tank for distilled water is made of rigid material, resistant to sunlight, of a capacity from 30 l to 60 l;
   the pump for distilled water installed at the base of the tank is a centrifugal pump;
   the tubes conveying the liquids or the samples is made of a flexible material resistant to sunlight;
   the irrigation nozzle for the sample collection container allows the spillage of the distilled water jet so that it is uniformly distributed on the collecting net of the material;
   the container for sample collection container is made of plastic material that is not altered by the materials collected in it;
   the filtering net has sufficiently dense meshes so as to avoid that, during the spraying cycle, the debris fall inside the sample collection container, together with the collected liquid, clogging the tubes or the nozzle for tube filler;
   the motion and level sensor applied to the sample collection container allows to generate alarms in the event of tampering with the system;
   the cylindrical test tubes container consists of a cylindrical vessel, in which are inserted a series of laboratory test tubes; optionally by a series of sensors in graphene; and by a rotating funnel equipped with two nozzles connected to a stepper motor;

the test tubes are of round cross-section and the center of the mouth of each tube is positioned at a predetermined distance to create a closed loop of tubes equidistant from one another;

the initial position of the rotating funnel provides that the filling nozzle is positioned at the center of the test piece No. 1 and that of irrigation for the sensors in graphene over sensor in graphene No. 1;

the movements of the stepper motor, contained in a waterproof box positioned at the top of the cylindrical test tubes container, are coordinated by the electronic control system;

the pump for sample collection is a self-priming pump, activated by the electronic control system;

the rotating funnel is connected directly to the shaft of the stepper motor and equipped with a nozzle for filling the test tube and a nozzle of irrigation for the sensors in graphene, if present;

at each sampling the electronic control system rotates the funnel, so that the nozzles are already positioned for the subsequent collection;

when the nozzle is positioned at the center of the test tube, the liquid sucked by the pump for collecting samples is transferred into the rotating funnel and from it through the nozzle ends up directly inside the test tube;

the water quality sensors made of graphene, if present, are made in a form, such as to allow assembly of the closed-loop sensors, exposing at the same time as much as possible graphene surface to the spraying liquid;

the sensors are electronically connected to the electronic control system of the black box;

the electronic control system is connected electronically to the system clock, to the stepper motor, the pumps and all the sensors;

the electronic system has the task of synchronizing all operations of collection and detecting and storing the data supplied by the sensors.

5. Method of use of the device of claim 1 or 3, wherein the black box comprises:

all safety and alarm configuration data are stored by the black box in permanent memories encrypted accessible only to the analyzers/certifiers bodies;

during initialization of the black box the device deletes all permanent memories, except for the safety memory, which will indicate timestamp of the initialization operation itself;

from the safety memory it is possible to check how many times and when the black box has been initialized;

once initialized, the black box is accessible via Wi-Fi on an encrypted communication channel;

all the data, samplings and alarms are collected in the black box;

the black box can be opened only by the certifier or the laboratory analyzing the samples through a burglar-proof mechanism to prevent and/or report illegal openings;

in the black box there are multiple test tubes that allow for multiple samplings, maintaining said samplings separated between each other;

at the end of the operative configuration the black box blocks the access for configuration and starts the normal control and operating cycle;

during the normal control and operating cycle the black box controls that the positions on the ground have not been modified, checks the availability of the test tubes and performs periodic measurements;

in case of alarms the black box becomes accessible for changes to configurations via Wi-Fi;

in case of alarms the black box also indicates optically the alarm condition by means of lights that indicate the type of alarm;

the black box indicates, through coloring and texture reported on an active surface, facing upward, the results of the quality measurements of the terrain or the microenvironment made through the sensors;

the geographical location of the black box, the colors, the textures and the data on quality measures, are directly detected by drones or satellites or transmitted via Wi-Fi and their diffusion occur, for example, through social networks, as a form of web applications;

in the presence of security alarms, the black box stores permanently in the alarm data secure storage, time and reason and it is set to receive a new consensus to operate;

in case one of the detectors/sensors of the device goes into alarm, the other sensors continue to provide reliable information and data, usable for the certification, which are stored by the black box;

in the presence the alarms for "the end tubes" or "emptying distilled water" or other, the system blocks its operation and is set to receive the consent after an operator has replenished the depleted assets, the cypher key being the one set at configuration time;

all the alarms are recorded in the safety memory;

during the normal measurement cycle, all the measurements carried out, both those associated with the test tubes and those, in which the sample is not deposited in test tubes, are stored on a permanent working memory which is canceled only during the initialization procedure.

6. Method of use of the device of claim 1, wherein the tube of distilled water placed in the sample collection container, the nozzle, the sample collection container, the filtering net and the opacity, acidity and bacteriological purity water sensors, the water collection pipe to be analyzed, the motion and level sensor, the data cable are duplicated, allowing the connection of multiple sensors for monitoring different points of the soil;

when more sensors are connected, the elements and are enriched/provided each with an electronic valve, controlled from the central element, to block the flow of water; wherein two further valves allow to put in direct communication the common parts; wherein such common parts of tube, before each measurement, are washed and placed in communication through the two electronic valves mentioned above, with the water of the tank; wherein the sensors are selected from the group consisting of: a sensor for the sampling, a sensor for pH detection, a sensor for detection of heavy metals and/or a sensor in graphene for the analysis of bacteriological purity of the water and/or opacity of the same;

wherein said sensors are protected from further movement and tilt sensors, which indicate changes of inclination or position that are stored by the system, as alarms, even visual, which allow to detect, which of the sampling or measurement sensor has been moved or tampered with.

7. Method of use of the device of claim 1, wherein:

it allows to automatically collect samples;

it controls and guarantees that the collection system has not been opened or tampered with;

it generates real time alarms and keeps track of them for the purpose of the organic product quality certification;

it allows to face in real or very short time, situations that could lead to degradation of production and the loss of quality certification.

8. Device of claim 1 for use for certifying the life cycle of an organic product chosen from the group consisting of vegetables, fruit, meat or fish farming product.

9. Device of claim 1 for use in collecting samples to be analysed:

for the pH and heavy metals measurement in water;
for the detection of phyto-hormones present in the soil;
for the detection of pesticides in the soil;
for the detection of growth hormones, antibiotics, bacteria, protozoa and viruses present in the litter of a breeding of animals;
for the detection in water of hormones, antibiotics/drugs and for the analysis of the "DNA" contained in the feed (dissolved/present in the water) used for the breeding of fish.

* * * * *